United States Patent
Yu et al.

(10) Patent No.: US 9,549,771 B1
(45) Date of Patent: Jan. 24, 2017

(54) FINGERSTALL-CANNULATED GUIDE FOR FAST AND ACCURATE GUIDE WIRE POSITIONING

(71) Applicants: Xiao Wei Yu, Shanghai (CN); Weiping Ren, Westland, MI (US); Emily Juan-Jie Ren, St. Louis Park, MN (US)

(72) Inventors: Xiao Wei Yu, Shanghai (CN); Weiping Ren, Westland, MI (US); Emily Juan-Jie Ren, St. Louis Park, MN (US)

( * ) Notice: Subject to any disclaimer, the term of this patent is extended or adjusted under 35 U.S.C. 154(b) by 568 days.

(21) Appl. No.: 14/092,987

(22) Filed: Nov. 28, 2013

(51) Int. Cl.
- A61B 17/88 (2006.01)
- A61B 17/17 (2006.01)
- A61B 17/84 (2006.01)
- A61B 17/16 (2006.01)
- A61B 17/00 (2006.01)
- A61B 17/90 (2006.01)

(52) U.S. Cl.
CPC ....... *A61B 17/8897* (2013.01); *A61B 17/1697* (2013.01); *A61B 17/17* (2013.01); *A61B 17/1764* (2013.01); *A61B 17/846* (2013.01); *A61B 17/848* (2013.01); *A61B 17/88* (2013.01); *A61B 2017/00438* (2013.01); *A61B 2017/90* (2013.01)

(58) Field of Classification Search
CPC . A61B 17/1697; A61B 17/17; A61B 17/1717; A61B 17/1721; A61B 17/175; A61B 17/1753; A61B 17/1757; A61B 17/1764; A61B 17/72; A61B 17/74; A61B 17/846; A61B 17/848; A61B 17/8897; A61B 2017/90; Y10T 403/7129; Y10T 403/7135
See application file for complete search history.

(56) References Cited

U.S. PATENT DOCUMENTS

| | | | |
|---|---|---|---|
| 4,726,371 A * | 2/1988 | Gibbens | A61B 17/3201 30/232 |
| 6,526,669 B2 * | 3/2003 | Nagata | A61B 5/1125 33/503 |
| 2002/0105797 A1 * | 8/2002 | Navid | B25B 23/18 362/120 |
| 2006/0173291 A1 * | 8/2006 | Glossop | A61B 90/96 600/424 |
| 2011/0092986 A1 * | 4/2011 | Gaynor | A61B 17/0482 606/139 |
| 2011/0092991 A1 * | 4/2011 | Gaynor | A61B 17/0401 606/148 |

(Continued)

*Primary Examiner* — Matthew Lawson
*Assistant Examiner* — Amy Sipp

(57) ABSTRACT

The present invention provides a fingerstall-cannulated guide device for accurate and efficient guide wire placement for antegrade femoral nailing systems. The said device comprises a fingerstall with a cannulated guide connected with or without a threaded guide wire. Using this device, surgeons can determine the entry point for the guide wire fast and accurately by tactile hand-eye coordination. After correct entry point is obtained, the guide wire is advanced and the fingerstall-cannulated guide can be easily detached. The device and method can accomplish the following: (1) reduction of the surgery time; (2) reduction of the radiation exposure times, and (3) reduction of the soft tissue damage during surgery. The device is also beneficial for use in fastening together any or all portions of bone surrounding a fracture site.

5 Claims, 6 Drawing Sheets shows the ways of using the fingerstall- cannulated guide for accurate guide wire positioning.

(56) References Cited

U.S. PATENT DOCUMENTS

2012/0123428 A1* 5/2012 Berberich .......... A61B 17/8866
                                                    606/96
2014/0100580 A1* 4/2014 Yu ..................... A61B 17/1697
                                                    606/96

* cited by examiner

Figure 3 shows the cannulated guide threaded with the guide wire.
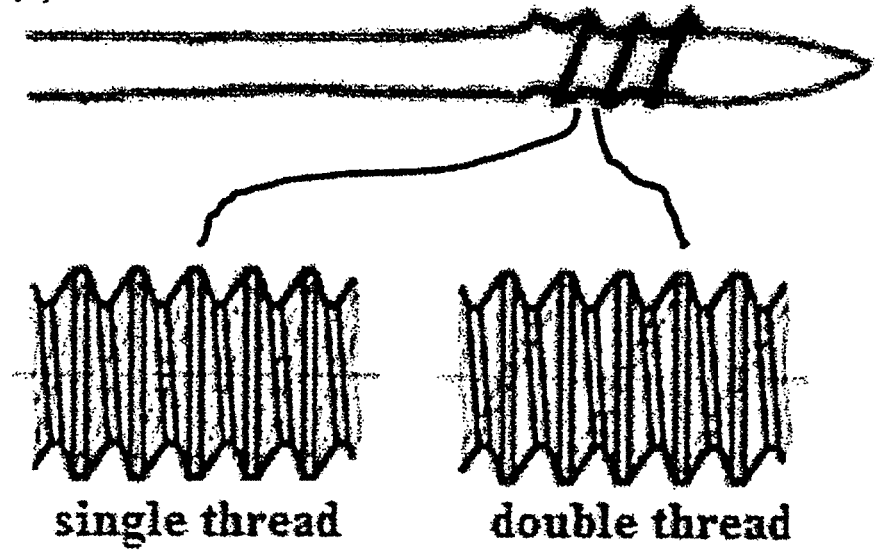
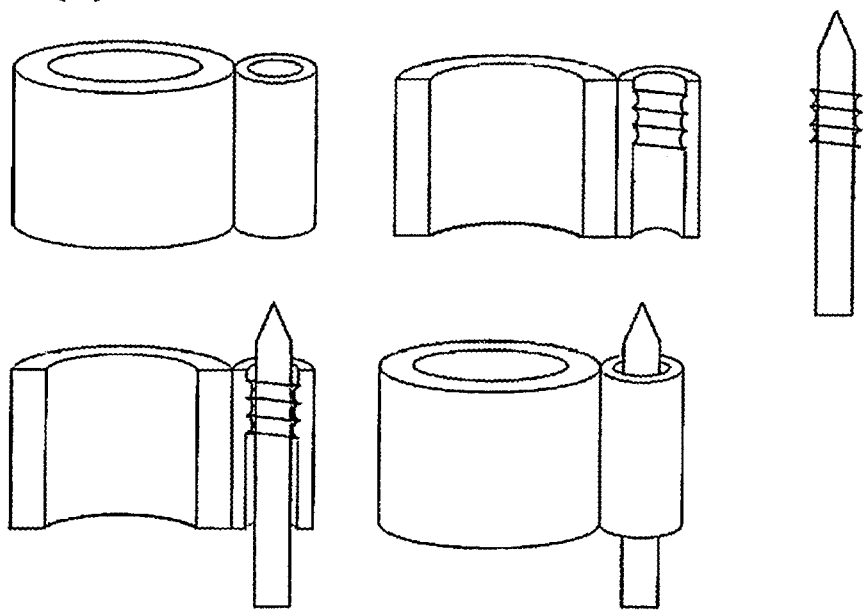

Figure 4 shows the ways of using the fingerstall- cannulated guide for accurate guide wire positioning.
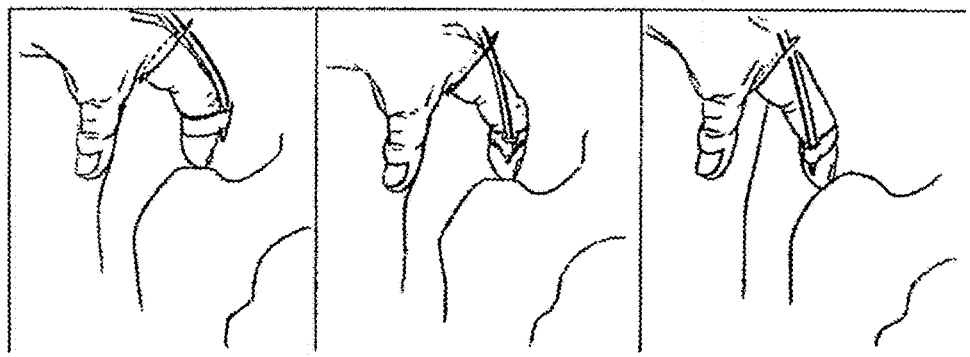

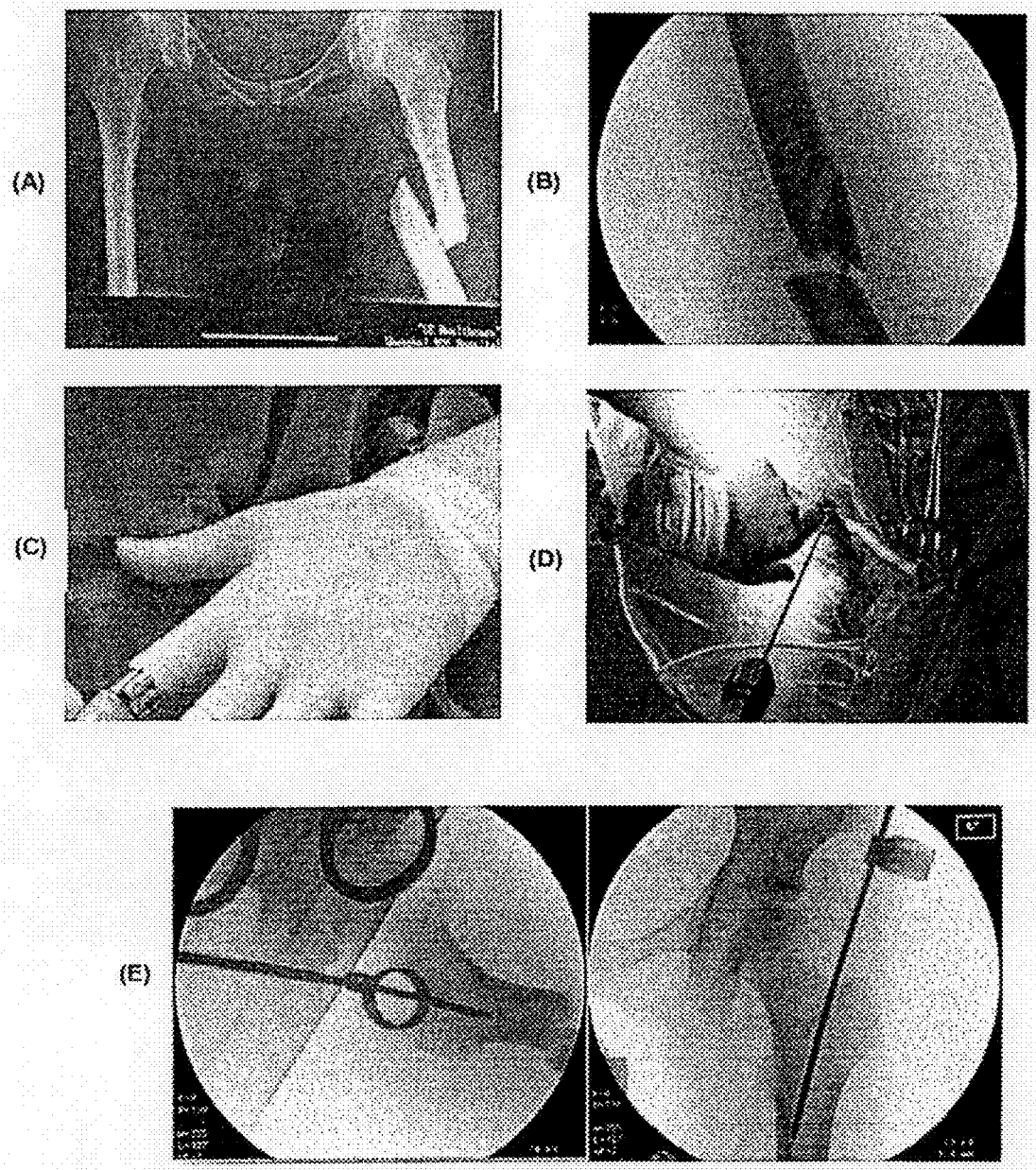

FINGERSTALL-CANNULATED GUIDE FOR FAST AND ACCURATE GUIDE WIRE POSITIONING

FIELD OF INVENTION

Figure 1:
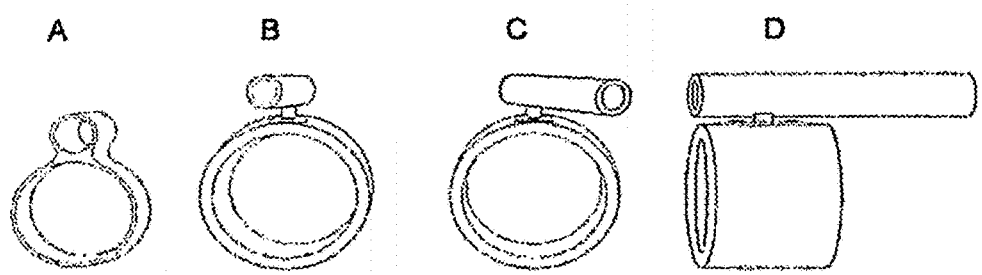
Figure 1 shows the device of the fingerstall with cannulated guide for guide wire positioning

The present invention relates to a fingerstall guide device for fast and accurate guide wire placement through the entry point during antegrade femoral nailing. The main objective of the present invention is to provide a simple and handy device for accurate positioning of guide wire efficiently with minimal to no x-ray exposure.

BACKGROUND ART

Find the entry point for the guide wire is one of the most crucial steps in antegrade intramedullary femoral nail placements. Guide wire positioning is usually done by trial and error method under C-arm image guidance. This method takes more time and does not give assurance of correct position of the entry point or trajection of the guide wire. It is always challenging to perform this guide wire positioning in minimum time with maximum accuracy.

Minimally invasive fracture fixation can be technically demanding, especially in body regions characterized by complex bony anatomy and the presence of a significant amount of soft tissue. Hence, this procedure is associated with a high risk of implant malposition. As a consequence, radiation exposure to the patient and the surgeon increases during surgery. Proximal femoral fractures are the second most common fracture in older patients and place a heavy demand on orthopedic departments worldwide. A short surgery time and use of less invasive approaches are the two key-parameters to reduce surgery related morbidity. In addition, an intramedullary nailing of proximal femoral fractures is often accompanied by increased radiation exposure time to control the implant placement [Chong K W, et al. Injury 2006; 37(8):755-762.]. The surgery should be least disruptive to the soft tissue envelope thus preserving blood supply and consequently better bone healing in poor quality osteoporotic bone. An added bonus will be to reduce the radiation exposure to the surgeon who is performing such operations on a regular basis.

A wide range of instruments could be subsumed from simple guiding drill sleeves to targeting tools adapted to the implant design [Krettek C, et al. Clinical Orthopedics and Related Research 1999; (364):267-275]. All of these devices are used to adjust an intended track and to hold a specific position of the guide wire until the implant is inserted. Such devices commonly require the surgeon to extrapolate the inner bony implant path using fluoroscopy in multiple planes that inevitably results in repetitive adjustment steps and drill trials. Hence, there is a need for simple and handy tools that allow a fast and accurate position of the guide wire entry point before intramedullary nail implantation.

The present invention provides the benefits on the reduction of radiation exposure, a decrease of procedure time, as well as a significant reduction of soft tissue envelope damage by a fast and accurate placement of guide wire through entry point.

BRIEF DESCRIPTION OF THE INVENTION

The present invention provides a fingerstall-cannulated guide device for accurate and fast guide wire positioning. The said device comprises a fingerstall with a cannulated guide pre-loaded with a guide wire. Using this device, surgeons can determine the entry point of guide wire insertion fast and accurately by hand-eye coordination. The guide wire is then detached from the cannulated guide by advancing the guide wire, and then the fingerstall-cannulated guide can be removed easily.

The surgeon's finger is used to feel for bony landmarks, including the greater trochanter and piriformis fossa, to correctly locate the desired entry point for guide wire insertion. The preferred trajectory of the guide wire can be adjustment both in the AP (anterior/posterior) and lateral planes using slight adjustments of the finger, using tactile and hand-eye coordination. Once the correct entry point and trajectory of the guide wire if obtained, the guide wire can be advanced into medullary canal with the free hand or by an assistant. After the guide wire is advanced, the fingerstall can be removed easily from the top of the fixed guide wire.

The fixed angle type of the cannulated guide is made by connecting the fingerstall to the cannulated guide by welding. The direction of the cannulated guide is in line to the fingerstall (i.e. parallel to the longitudinal axis of the finger). The rotary type of the cannulated guide is made by mounting a rotating head-attached cannulated guide into the outer cylindrical grooves of the fingerstall and by bulkhead screws. The rotating head can rotate freely. Alternatively, the rotation of the rotary head can be finely controlled by the setting in the range from 0 to 360° C.

The cannulated guide can either be threaded to facilitate pre-loading the guide-wire. The length and the position of the threaded surface of a guide wire is adjustable and can be at the position of 2 cm from the tip of the guide wire being inserted. The position of the threaded guide wire surface can be adjusted according to the local tissue geometry and anatomic structures. Alternatively, the inner wall of the cannulated guide can be non-threaded/smooth for guide wire insertion.

The fingerstall is in line with the attached guide wire though attached cannulated guide connection. This design can avoid the potential injury to the surgeon's fingers when advancing the guide wire into the bone tissues.

The present invention provides the benefits on the reduction of radiation exposure, a decrease of procedure time, as well as a significant reduction of soft tissue envelope damage by a fast and accurate placement of guide wire. More specifically, the advantages of the device are: (1) metal device to be sterilized easily; (2) an increased incision is not required because the small size of the device; (3) a fast, accurate and reliable positioning of the guide wire is directly controlled by the tactile and hand-eye coordination, and (4) can be used as a guide for intramedullary nailing systems, as well as for the temporarily or final fixation of the bone fracture. Therefore, operation time can be significantly reduced, unnecessary bone damage or infection of a patient can be prevented and a patient and/or surgeon's exposure to X-ray radiations can be considerably reduced.

BRIEF DESCRIPTION TO THE FIGURES

Figure 2:
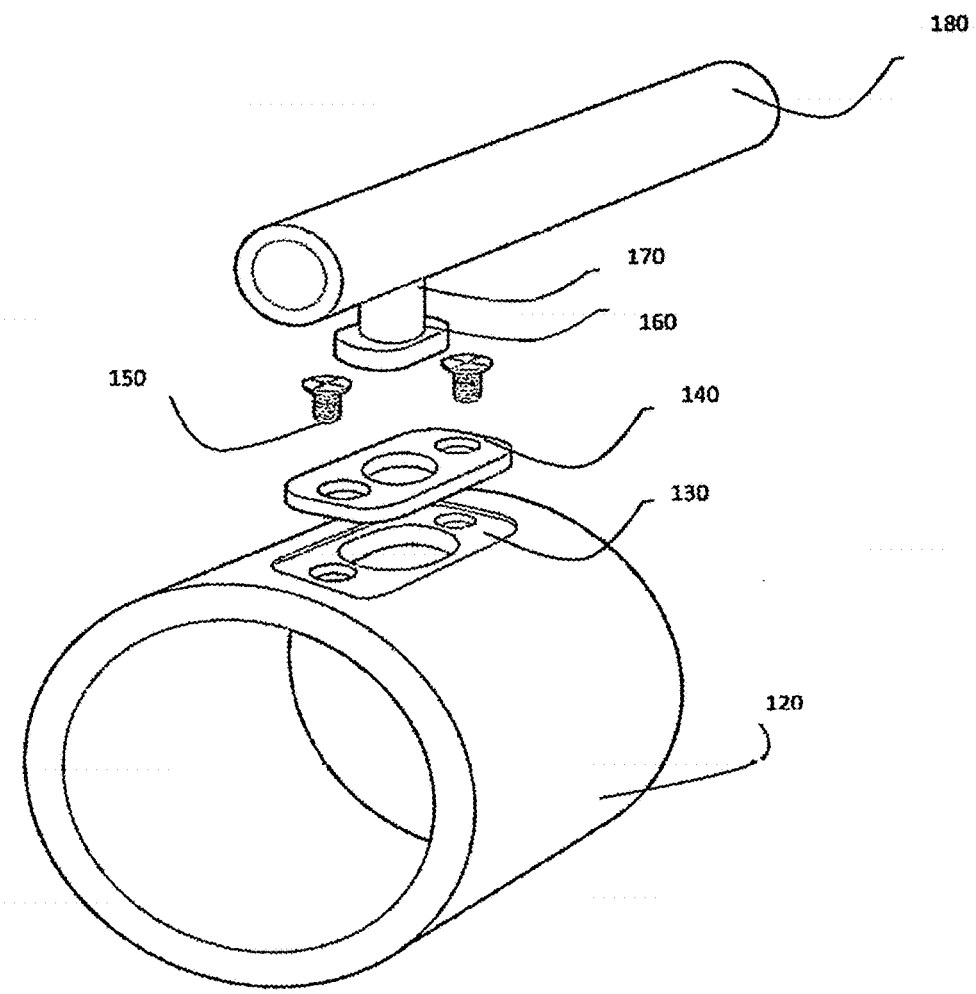
Figure 2 shows the construction of fingerstall with rotatable angle cannulated guide
Figure 2:
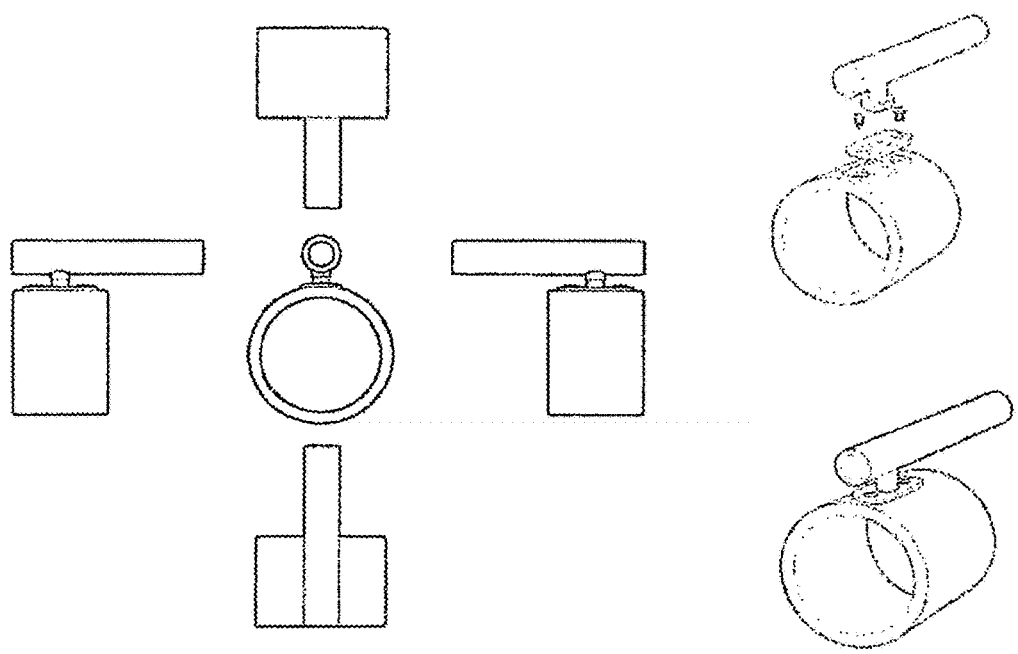

By way of example, preferred embodiments of the invention are described with reference to the accompanying drawings in which:

FIG. 1 describes the device of the fingerstall-cannulated guide for guide wire positioning FIG. 2 shows the construction of fingerstall with rotatable angle cannulated guide FIG. 3 shows the cannulated guide threaded with the guide wire.

FIG. 4 shows the ways of using fingerstall-cannulated guide for accurate guide wire positioning.

FIG. 5 shows an example of femur fracture fixation using fingerstall-cannulated guide.

DETAILED DESCRIPTION OF THE DRAWINGS

The present invention is illustrated by way of prototype products, in the figures of the accompanying drawings.

FIG. 1 describes the construction of fingerstall and the cannulated guide. The fingerstall can be made of metal and/or other materials. The inner diameter of the fingerstall can be any size that can fit the fingers of the surgeons (any fingers from both hands). The length of the fingerstall can be varied and has no interference with the free movement of the finger joints during operation. In addition, the fingerstall can be fully enclosed or semi-enclosed. The cannulated guide can be made of metal and/or any other materials. The inner diameter of the fingerstall is between 2 mm and 5 mm or any size that can fit the diameter of guide wire being used. The length of the cannulated guide can vary based on the real requirement of various types of surgery. The axial direction of the cannulated guide is in line with the fingerstall. The fingerstall is connected with either a fixed-angle (A) or rotatable cannulated guide (B-D). The outer wall of the cannulated guide is fixed to the fingerstall by welding in the fixed type (A). In the rotatable type, the cannulated guide with a rotary head is assembled with the fingerstall by a bulkhead and screw fixation (See FIG. 2).

FIG. 2 describes the construction of fingerstall with rotatable angle cannulated guide.

FIG. 2A demonstrates the assembly of rotatable angle cannulated guide. This device is composed of these parts: (a) cannulated guide projected with a rotary head underneath (3); (b) bulkhead (2) is used to connect the rotary head with the fingerstall; (c) fingerstall (1) with outer cylindrical grooves for rotary head insertion though the bulkhead and screw fixation, and (d) screws (4) (whole thread flat head) are used to fix the bulkhead to the outer cylindrical grooves of fingerstall FIG. 2B demonstrates the different views of the assembled fingerstall with rotatable angle cannulated guide.

FIG. 3 shows the cannulated guide threaded with the guide wire.

As shown in FIG. 3A, the tip of the guide wire is threaded. The number, pattern and the depth of the threads are matched with the threaded cannulated guide, so the guide wire is connected within the cannulated guide before use or pre-packed. Usually, the length of the threaded surface can be 100~500 mm with 3-4 rings thread (single thread or double thread pattern).

FIG. 3B demonstrates the design of the threaded cannulated guide. The inner wall of the cannulated guide is threaded (partially or totally) with the various numbers of threads (3 and up). Alternatively, the inner wall of the cannulated guide can be smooth and no guide wire is attached. The un-threaded guide wire can be inserted into the cannulated guide during operation.

FIG. 4 shows the ways of using fingerstall-cannulated guide for accurate guide wire positioning. Fingerstall-cannulated guide means nimble fingers, directly connected with the tip of the guide wire, provide much easier ways to control the direction of the guide wire during operation. As shown in FIG. 5, the surgeon puts his/her index finger on the surface of greater tuberosity of the femur, and adjusts the position of his finger (via the finger interphalangeal joint flexion) to control the accurate angle and position of the guide wire to the bone surface. Second adjustment of the guide wire position is usually not required.

FIG. 5 shows an example of femur fracture fixation using fingerstall-cannulated guide.

(a) Femur stem fracture is confirmed by radiograph.
(b) Reduction of the fracture is approached by traction.
(c) Surgeon wears a fingerstall-cannulated guide on his left index finger.
(d) First, the threaded guide wire is manually screwed into the threaded cannulated guide and the top end of the guide wire is connected with a drill. Then, surgeon puts his left index finger together with the fingerstall-cannulated guide on the surface of greater tuberosity of the femur, and adjusts the position of his finger to control the accurate angle and position of the guide wire to the bone surface though the hand-eye coordination. Then insert the guide wire into the bone structure by drilling using the right hand. Since the guide wire is detached from the cannulated guide by drilling, and then the fingerstall-cannulated guide can be removed easily from the top of the inserted guide wire before radiograph.
(e) A satisfactory position of one-step guide wire insertion was confirmed by conventional radiographic examination. The entire procedure can be completed by one surgeon. The duration of each surgical step, the radiation exposure time, as well as the number of radiation images is reduced.

What is claimed is:

1. A fingerstall-cannulated guide device comprises: a fingerstall attached with a cannulated guide with or without a threaded guide wire wherein the cannulated guide is made of metal and/or other materials, an inner diameter of the fingerstall is between 2 mm and 5 mm, a length of the cannulated guide can vary, and the cannulated guide can be rotatable; and wherein the rotatable cannulated guide comprises the cannulated guide connected with a rotating head and mounting parts to fix the rotating head to the fingerstall; wherein the mounting parts comprise an outer cylindrical fingerstall groove for rotating head insertion, a bulkhead, and screws.

2. The device of claim 1, wherein the fingerstall is made of metal and/or other materials; an inner diameter of the fingerstall is sized to fit fingers of a surgeon; and a length of the fingerstall is sized such that there is no interference with free movement of finger joints during operation.

3. The device of claim 1, wherein a shape of the fingerstall is round or oval, or any other types, and the fingerstall can be fully enclosed or semi-enclosed.

4. The device of claim 1, wherein an inner wall of the cannulated guide can be partially or totally threaded for attachment of the guide wire before use the inner wall of the cannulated guide can be smooth and no guide wire is attached and the guide wire can be inserted into the cannulated guide during operation.

5. A fingerstall-cannulated guide device comprises: a fingerstall attached with a cannulated guide with or without a threaded guide wire inside; wherein the cannulated guide is made of metal and/or the other materials, and inner diameter of the fingerstall is between 2 mm and 5 mm, a length of the cannulated guide can also vary, and the cannulated guide can be rotatable; and wherein a rotating head can rotate freely or the rotation can be finely controlled by a setting in a range from 0 to 360° C.

* * * * *